United States Patent [19]

Kuehn et al.

[11] Patent Number: 5,201,654
[45] Date of Patent: Apr. 13, 1993

[54] DENTAL HOSE CLEANING METHOD AND APPARATUS

[75] Inventors: Paul Kuehn, Eau Clair, Wis.; Thomas A. Lansing, Pine Springs, Minn.

[73] Assignee: Pinnacle Products, Inc., Eau Claire, Wis.

[21] Appl. No.: 678,798

[22] Filed: Apr. 1, 1991

[51] Int. Cl.$^5$ .................... A61C 17/06; A61C 17/14
[52] U.S. Cl. ........................... 433/25; 433/91; 433/229
[58] Field of Search ............... 433/91, 92, 229, 25; 422/28, 33; 222/211, 481.5

[56] References Cited

U.S. PATENT DOCUMENTS

| | | | |
|---|---|---|---|
| 1,353,587 | 9/1920 | Heck | 433/92 |
| 2,219,208 | 10/1940 | Knight | 222/211 |
| 3,396,762 | 8/1968 | Paton | 422/28 X |
| 3,756,470 | 9/1973 | Bagwell et al. | 222/481.5 X |
| 3,777,403 | 12/1973 | Ritchie | 433/92 |
| 4,024,992 | 5/1977 | Schmid | 222/211 |
| 4,526,622 | 7/1985 | Takamura et al. | 422/33 X |
| 4,579,597 | 4/1986 | Sasa et al. | 422/33 X |
| 4,700,861 | 10/1987 | Neward | 222/211 X |
| 4,782,985 | 11/1988 | Kinsley | 222/481.5 |
| 5,044,953 | 9/1991 | Sullivan | 433/91 X |

FOREIGN PATENT DOCUMENTS 3423836 1/1986 Fed. Rep. of Germany ........ 433/92
3900108 7/1990 Fed. Rep. of Germany ........ 433/91

OTHER PUBLICATIONS

Instructions for Vacusol Cleanser System.
Advertising brochure entitled "Vacuum System Decontamination by Biotrol International".

Primary Examiner—John G. Weiss
Assistant Examiner—Nicholas D. Lucchesi
Attorney, Agent, or Firm—Foley & Lardner

[57] ABSTRACT

Apparatus for cleaning hoses used by a dentist in the course of his work has a container having a mouth and a top adapted to snugly cover the mouth of the container. The top includes at least one nozzle protruding upwardly from a surface of the top to the exterior of the container, the nozzle having an internal bore through which fluid in the container may pass and the nozzle sized to fit snugly within a hose attachment attached to the end of an external suction hose so that the hose may be connected to the nozzle via the hose attachment. The top also includes an internal tube attached firmly to the nozzle and extending into the lower interior portion of the container, so that the unattached end of the internal tube is immersed in the fluid. The application of suction to the external suction hose causes the fluid in the container to be drawn through the internal tube, the nozzle, and then the hose, thereby cleaning the hose with the fluid.

20 Claims, 2 Drawing Sheets

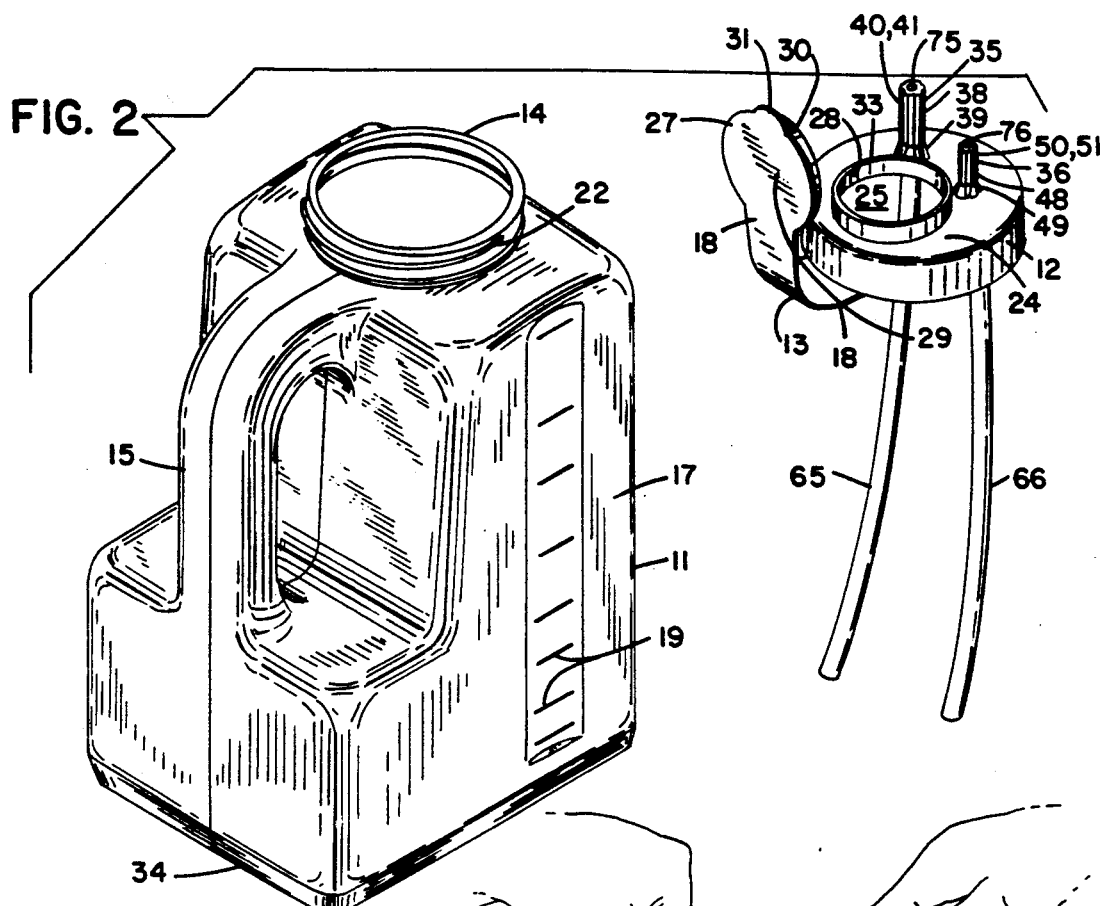
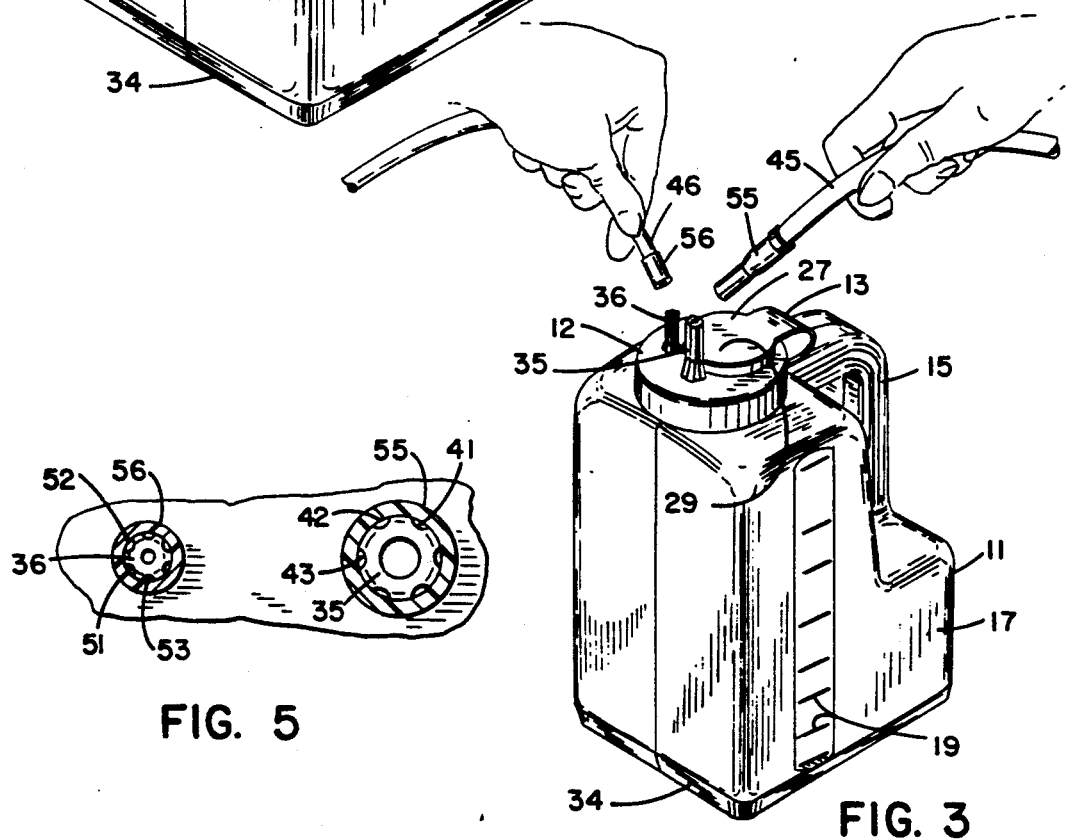

DENTAL HOSE CLEANING METHOD AND APPARATUS

FIELD OF THE INVENTION

This invention relates generally to hose cleaning apparatus and particularly to apparatus used to clean suction hoses used by a dentist in the course of his work on a patient.

BACKGROUND OF THE INVENTION

In the course of a dentist's treatment of a patient, the dentist uses both high volume and low volume suction hoses to remove saliva and waste particles from a patient's mouth. Over time, bacteria, fungus and residual matter can build up in these hoses and possibly clog them. Moreover, since the hoses work in combination with other dental office equipment, residual build-up in the hoses can result in damage to the remainder of the equipment. Greater residual build-up exposes dental patients to an increased risk of contact with infectious materials because some of the residual matter could back up within the hoses.

Previous methods for cleaning hoses used in a dentist's office involve placing a free end of a hose directly into a container of cleaning fluid and applying suction to the other end of the hose. The application of the suction draws the fluid through the hose, thereby cleansing it. This method of cleaning hoses can create several problems. Much spillage of cleaning fluid results if the container accidently tips over during the procedure. In addition, the hose may not remain engulfed in the cleaning fluid as the suction application progresses. Finally, this method can be quite time-consuming, as the engulfed end of the hose must be thoroughly wiped off following the completion of the procedure.

SUMMARY OF THE INVENTION

The present invention provides an efficient and economical method of cleansing hoses used in the course of a dentist's work, thereby minimizing staff and patient contact with infectious materials. In accordance with the present invention, a hose cleaning apparatus is constructed so that two hoses can be easily connected to the apparatus and cleaned in a matter of minutes. More specifically, the apparatus is adapted to clean the high and low volume suction hoses used by a dentist in working on a patient. The apparatus is comprised of a container having a mouth and a top adapted to snugly cover the mouth of the container. The container is filled with cleaning fluid, a portion of which is eventually drawn out of the apparatus and through the hoses, thereby cleaning them. The top preferably includes two cylindrical nozzles protruding upwardly from a flat surface of the top, each nozzle having an internal bore which permits fluid to pass through one end of the nozzle and out of the other end. Each nozzle is adapted to receive an external suction hose, one a high volume suction (HVS) hose and the other a low volume suction (LVS) hose, whereby the external suction hoses fit snugly over the nozzles. A separate internal tube is attached firmly to each nozzle, each internal tube extending from the nozzle to the lower interior portion of the container so that the unattached end of the internal tube is immersed in the cleaning fluid. These internal tubes extend to such a depth within the container that they are able to remain engulfed in the cleaning fluid until virtually no fluid remains in the container. Thus, no interruptions will occur in the hose cleaning process due to an inability to draw in fluid, unless, of course, the container is virtually empty.

The hose cleaning apparatus operates in the following manner. First, the container is filled with about one to four quarts of cleaning fluid. Second, the two external suction hoses are connected to the hose cleaning apparatus via the hose attachments. The HVS hose is connected to the apparatus by fitting the HVS attachment over the HVS nozzle, and the LVS hose is connected by fitting the LVS attachment over the LVS nozzle. Finally, suction is applied simultaneously or separately to the HVS hose and the LVS hose, thereby drawing the cleaning fluid out of the container and through the hoses.

While suction is applied, the hose cleaning apparatus remains upright. If the apparatus is accidently tipped over during the hose cleaning process, spillage is limited to the volume of fluid contained in the two internal tubes of the apparatus.

Further objects, features and advantages of the invention will be apparent from the following detailed description when taken in conjunction with the accompanying drawings.

BRIEF DESCRIPTION OF THE DRAWINGS

In the drawings:

FIG. 2 is a perspective view of the hose cleaning apparatus of FIG. 1, with the container and the top separated from each other.

FIG. 3 is a perspective view of the hose cleaning apparatus of FIG. 1, the two hose attachments of the two external suction hoses in the process of being placed over their respective nozzles.

FIG. 5 is a section view taken on line 5—5 of FIG. 4.

DETAILED DESCRIPTION OF THE INVENTION

Figure 1:
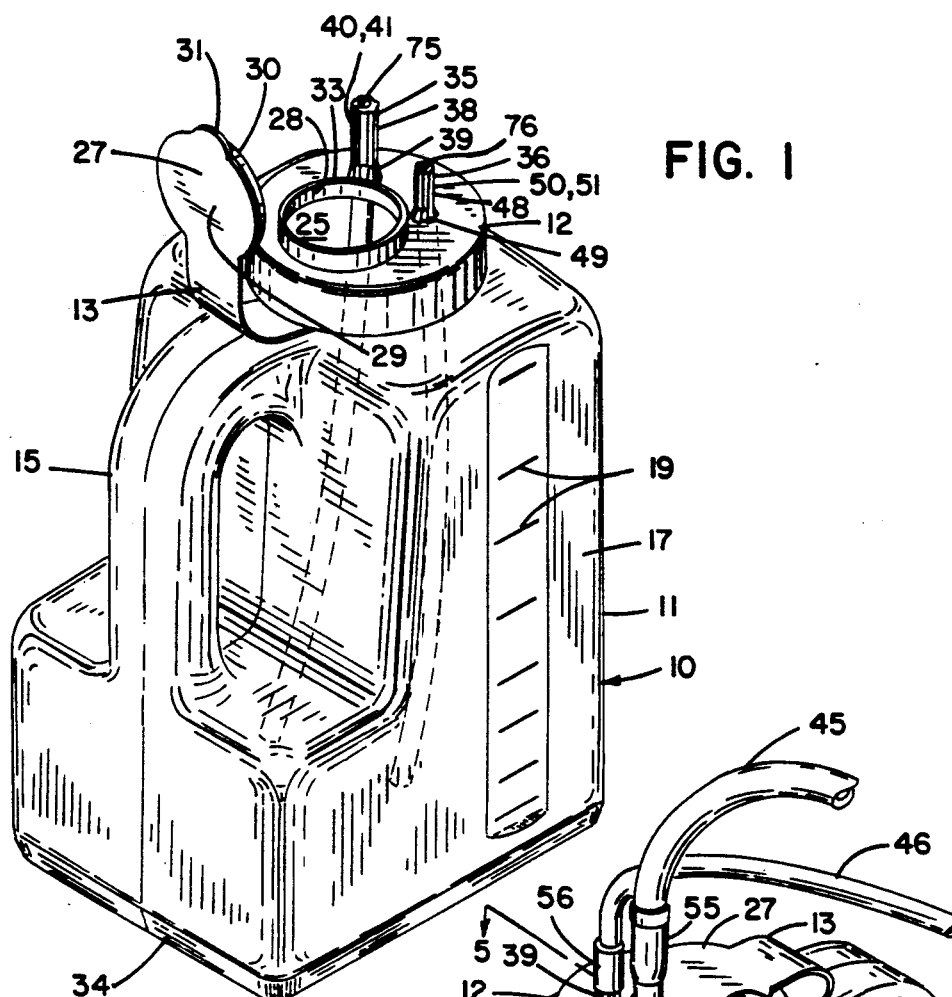
FIG. 1 is a perspective view of the hose cleaning apparatus of the present invention.

With reference to the drawings, FIG. 1 illustrates the hose cleaning apparatus of the present invention, which is preferably used for cleaning the high and low volume suction hoses in a dentist's office. The hose cleaning apparatus, generally referred to by reference numeral 10, includes a container 11 for holding cleaning fluid and a top 12, the container having a mouth 14 over which the top 12 is placed to close and seal the container 11.

FIG. 2 depicts the container 11 and the top 12 separated from each other. In the preferred embodiment the container 11 is shaped like an "L" with a handle 15 integrally connected between the legs of the L-shaped container 11. The handle 15 is preferably shaped like a half-arch which extends between the legs of the container 11. The handle 15 is sized so that it can be easily grasped by one's hand, thereby making it easy to carry the apparatus 10 from one place to another. Preferably, the handle 15 is hollow, thereby allowing fluid to enter the handle 15 when the level of fluid in the container 11 reaches the height of the handle 15, where the container 11 is standing upright. In other words, the handle 15 contributes to the overall volume of fluid which can be carried in the container 11.

Figure 4:
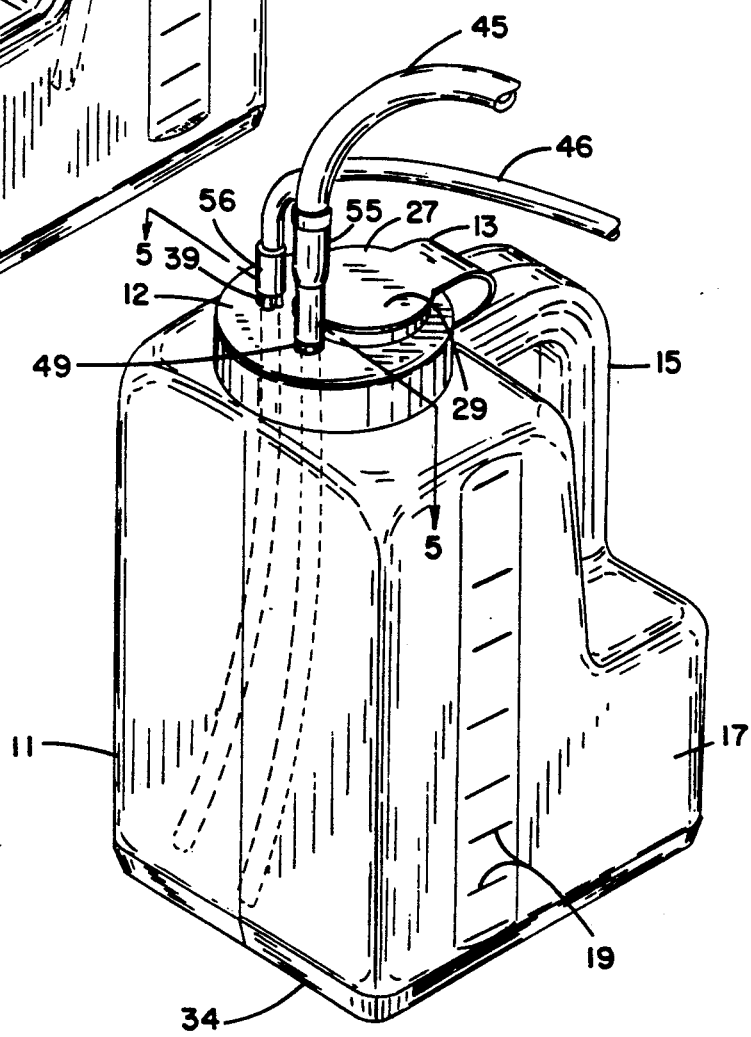
FIG. 4 is a perspective view of the hose cleaning apparatus of FIG. 1, the hose attachments of the two external hoses having been placed over the nozzles so that the hose cleaning process may begin.

In the preferred embodiment, sides 17 of the container 11, depicted in FIGS. 1–4, include level markers 19. Each marker is labelled to indicate the volume of fluid in the container 11 when the container 11 is filled to the height of the marker. The markers 19 on the side 17 shown in FIGS. 1 and 2 are labeled in metric units, while the markers on the side 17 shown in FIGS. 3 and 4 are labeled in English units. Due to the irregular shape of the container 11, the markers 19 form a non-linear scale (i.e., the markers are not evenly spaced). For purposes of exemplification, the markers on the side labeled in metric units are at levels indicating a container volume which is a multiple of 500 ml. (i.e., 0.5 liters), the highest marker indicating a volume of 4 liters and the lowest marker indicating a volume of 500 ml. The markers on the side labeled in English units are at levels indicating a container volume which is a multiple of 16 oz. (i.e., 0.5 quarts), the highest marker indicating a volume of 1 gallon (i.e., 4 quarts) and the lowest marker indicating a volume of 16 oz. The container is preferably formed of a somewhat transparent or translucent plastic, so that the level of the contents of the container can be observed through the walls of the container.

FIG. 2 illustrates the top 12 separated from the container 11. The top is adapted to snugly cover the mouth 14 of the container 11. In the preferred embodiment, the top 12 has threads for screwing the top 12 onto the container mouth 14, the mouth 14 having threads 22 onto which the top 12 is screwed. When the top 12 is placed over the mouth 14 of the container 11, rotation of the top 12 in one direction rotates the top 12 onto the threaded mouth 14 to close and seal the container 11, and rotation of the top 12 in an opposite direction causes the top 12 to be loosed from the mouth 14.

In the preferred embodiment, a flat surface 24 of the top 12 defines a circular aperture 25 such that the container 11 may be filled with fluid in either of two ways. First, when the container 11 is not sealed closed by the top 12, fluid may be added to the container 11 through the mouth 14 of the container 11. Second, when the container 12 is sealed closed by the top 12, fluid may be added to the container 11 through the aperture 25 in the top 12. To prevent the fluid from escaping through the aperture 25 if the hose cleaning apparatus 10 is tipped over, the top 12 further includes a circular cap 27 adapted to cover the aperture 25 in the top 12. In the preferred embodiment, the cap 27 seals the aperture 25 by a resilient snapping engagement of a lip 28 surrounding and extending upwardly from the aperture 25. The cap 27 includes a planar portion 29 and a cylindrical surface 30 integrally connected to and extending downwardly from the planar portion 29, the cylindrical surface 30 having a gradually decreasing inside diameter where the smallest diameter is located at a bottom cylindrical portion 31 which engages the lip 28 first. The lip 28 has a gradually increasing outside diameter where the largest diameter is located at an uppermost portion 33 of the lip 28. In order for the aperture 25 to be sealed by a resilient snapping engagement, the outside diameter at the uppermost portion 33 of the lip 28 must be slightly greater than the inside diameter at the bottom cylindrical portion 31 of the cap 27, such that the application of a moderate amount of downward force to the cap 27 when placed over the lip 28 of the aperture 25 causes the resilient engagement of the lip 28 of the aperture 25. In the preferred embodiment, the cap 27 and the top 12 are hingedly interconnected by an integrally formed hinge strap 13 at the ends 18 thereof as best shown in FIGS. 1 and 2. The hinge strap 13 must be of sufficient length to allow the cap 27 to be placed on and taken off of the lip 28 of the aperture 25. In addition, the planar portion 29 of the cap 27 preferably includes an extension 31 which allows for easy removal of the cap 27 from the lip 28 by applying upward force to the extension 31. Although the apparatus 10 shown in the drawings is used in conjunction with a cap 27 which resiliently engages a lip 28 to thereby seal the aperture 25, the apparatus 10 of the present invention could also be used in combination with a cap 27 which seals the aperture 25 in another manner, such as by engagement of threads on the cap with other threads on the lip.

As depicted in FIGS. 1–4, the top 12 preferably includes two cylindrical nozzles, 35 and 36, protruding upwardly from the flat surface 24 of the top 12. Each nozzle 35 and 36 has an internal bore, 75 and 76 respectively, extending through the entire length of the nozzle so that fluid can pass through one end of the nozzle and out the other end. As depicted in FIGS. 3 and 4, the high volume suction (HVS) nozzle 35 is adapted to receive an HVS attachment 55 which is attached to the end of an external HVS hose 45. A cylindrical upper portion 38 of the HVS nozzle 35 has an outside diameter substantially the same as or slightly smaller than the inside diameter of the HVS attachment 55, thereby allowing the HVS attachment 55 to fit snugly over the HVS nozzle 35. Preferably, a lower portion 39 of an outer surface 40 of the HVS nozzle 35 is widened in a radially outward direction to the flat surface 24 of the top 12, such that the HVS attachment 55 does not encase the lower portion 39 of the HVS nozzle 35.

Similarly, the low volume suction (LVS) nozzle 36 is adapted to receive an LVS attachment 56 which is attached to the end of an external LVS hose 46. A cylindrical upper portion 48 of the LVS nozzle 36 has an outside diameter substantially the same as or slightly smaller than the inside diameter of the LVS attachment 56, thereby allowing the LVS attachment 56 to fit snugly over the LVS nozzle 36. Preferably, a lower portion 49 of an outer surface 50 of the LVS nozzle is widened in a radially outward direction to the flat surface 24 of the top 12, such that the LVS attachment 56 does not incase the lower portion 49 of the LVS nozzle 36.

As shown in the FIGS. 1–4, a flexible plastic internal tube is attached firmly to each nozzle, the internal HVS tube 65 being attached to the HVS nozzle 35 and the internal LVS tube 66 being attached to the LVS nozzle 36. Each internal tube extends from the corresponding nozzle to the lower interior portion of the container 11. Preferably, each internal tube terminates close to the bottom 34 of the container 11 at a height below the height of the lowest level markers, the lowest marker on the side 17 labelled in metric units indicating a container volume of 500 ml. and the lowest marker on the side 17 labelled in English units indicating a container volume of 16 oz. For example, the internal tubes, which are preferably formed of somewhat flexible plastic, may be formed long enough to reach the bottom of the container and be bent slightly. Cleaning fluid in the container 11 may be drawn through the internal tubes 65 and 66, the suction nozzles 35 and 36, and the external suction hoses 45 and 46 by applying suction to the external suction hoses which are connected to the usual suction equipment.

In the preferred embodiment, the hose cleaning apparatus 10 operates in the following manner. With the cap 27 opened, as depicted in FIG. 1, cleaning fluid is added to the container 11. The cleaning fluid may be either poured or pumped into the container 11. Unless the cleaning fluid has been diluted by combining it with water prior to adding the fluid to the container 11, water must be added to the open cap 27 to dilute the concentrated fluid. For example, 1–4 oz. of concentrated fluid should be diluted to an appropriate level of 1–4 quarts. The markers 19 on the container 11 indicate the fluid level in English and metric units. The cap 11 is replaced after the fluid has been added to the container 11. Alternatively, the fluid may be added to the container 11 directly through the mouth 14 with the top 12 unscrewed, as illustrated in FIG. 2. After the fluid is properly diluted, the top 12 is screwed onto the container 11 and the cap 27 is snapped shut.

Next, as depicted in FIGS. 3 and 4, the external suction hoses 45 and 46 are connected to the hose cleaning apparatus 10 via the hose attachments 55 and 56 by fitting each attachment over the appropriate nozzle. The HVS hose 45 is connected to the apparatus 10 by placing the HVS attachment 55 over the HVS nozzle 35, so that the entire nozzle 35 is encased within the HVS attachment 55 with the exception of the lower portion 39 of the HVS nozzle 35. Similarly, the LVS hose 46 is connected to the apparatus 10 by placing the LVS attachment 56 over the LVS nozzle 36, so that the entire nozzle 36 is encased within the LVS attachment 56 with the exception of the lower portion 49 of the LVS nozzle 36.

Finally, suction is applied simultaneously or separately to the HVS hose 45 and the LVS hose 46, thereby drawing the cleaning fluid out of the container 11 and through the hoses. In the preferred method, the suction is applied long enough for the high volume suction to remove approximately 1 quart of solution, a time ranging from 45–60 seconds. The hose cleaning apparatus 10 remains upright, as illustrated in FIGS. 1–4, while suction hoses are applied.

As depicted in FIG. 5, the outer surface 40 of the HVS nozzle 35 includes axially-oriented grooves 41 extending through the entire length of the HVS nozzle 35. Due to these grooves 41, the outer surface 40 of the HVS nozzle 35 does not mate perfectly with the inside surface 42 of the HVS attachment 55. Instead, air gaps 43 are formed where the grooves 41 prevent the surfaces 40 and 42 from abutting against one another. When suction is applied to the HVS hose 45, not only is fluid drawn out of the container 11 and through the HVS hose 45, but some air from the exterior of the container 11 is sucked through the gaps 43 and into the HVS hose 45. Since the grooves 41 extend through both the upper portion 38 and the lower portion 39 of the HVS nozzle 35 and the HVS attachment 55 does not incase the lower portion 39, the gaps 43 are not obstructed where air initially enters the HVS attachment 55. The slight air intake agitates the fluid being drawn through the HVS hose 45, thereby improving the effectiveness of the cleaning process.

Similarly, the outer surface 50 of the LVS nozzle 36 includes axially-oriented grooves 51 extending through the entire length of the LVS nozzle 36. Due to these grooves 51, the outer surface 50 of the LVS nozzle 36 does not mate perfectly with the inside surface 52 of the LVS attachment 56. Instead, air gaps 53 are formed where the grooves 51 prevent the surfaces 50 and 52 from abutting against one another. When suction is applied to the LVS hose 46, not only is fluid drawn out of the container 11 and through the LVS hose 46, but some air from the exterior of the container 11 is sucked through the gaps 53 and into the LVS hose 46. Since the grooves 51 extend through both the upper portion 48 of the LVS nozzle 36 and the LVS attachment 56 does not encase the lower portion 49, the gaps 53 are not obstructed where air initially enters the LVS attachment 56. The slight air intake agitates the fluid being drawn through the LVS hose 46, thereby improving the effectiveness of the cleaning process.

From the above description, many variations in the described hose cleaning apparatus of this invention will be apparent to those skilled in the art. It is understood that the invention is not limited to the embodiments set forth herein as illustrative but embraces such modified forms thereof as come within the scope of the following claims.

What is claimed is:

1. An apparatus for cleaning hoses used in the course of a dentist's work, comprising:
   (a) a container having a mouth through which fluid may be added to the container; and
   (b) a top adapted to snugly cover the mouth of the container, the top having
      (i) two nozzles protruding upwardly from a surface of the top to the exterior of the container, comprising a high volume suction (HVS) nozzle adapted to receive an HVS attachment which is attached firmly to the end of an external HVS hose, so that the HVS attachment fits snugly over the HVS nozzle, and a low volume suction (LVS) nozzle adapted to receive an LVS attachment which is attached firmly to the end of an external LVS hose, so that the LVS attachment fits snugly over the LVS nozzle, wherein suction may be applied simultaneously or separately to the HVS hose and the LVS hose, each nozzle having an internal bore through which fluid in the container may pass,
      (ii) a hollow internal tube attached firmly to each nozzle and extending into the lower interior portion of the container and terminating close to the bottom of the container, such that fluid may be drawn by suction through each internal tube and the nozzle to which it is attached,
      (iii) wherein the top has a surface with an aperture therein such that the container may be filled with fluid either by adding fluid through the mouth of the container or by adding fluid through the aperture in the top, and
      (iv) a cap sized and adapted to close the aperture in the top and to be released therefrom to allow the container to be filled through the aperture in the top.

2. The apparatus of claim 1 wherein the container includes a handle for carrying the apparatus.

3. The apparatus of claim 1 wherein the container includes markers on the side of the container, each marker being labelled to indicate the volume of fluid in the container when the container is filled to the height of the marker.

4. The apparatus of claim 1 wherein the top has threads for screwing the top onto the container mouth and the mouth has threads adapted to receive the threads on the top, so that rotation of the top in one direction rotates the top onto the threaded mouth to close and seal the container, while rotation of the top in an opposite direction causes the top to be loosed from the mouth.

5. The apparatus of claim 1 further including
   (a) a lip surrounding and extending upwardly from the aperture, the lip having a gradually increasing outside diameter where the largest diameter is located at an uppermost portion of the lip;
   (b) wherein the cap has a planar portion and a cylindrical surface integrally connected to and extending downwardly from the planar portion, the cylindrical surface having a gradually decreasing inside diameter where the smallest diameter is located at a bottom cylindrical portion which engages the lip first; and
   wherein the largest outside diameter of the lip is slightly greater than the smallest inside diameter of the cylindrical surface of the cap so that the application of a moderate amount of a downward force to the cap when placed over the lip of the aperture causes resilient engagement of the lip.

6. The apparatus of claim 1 further including a hinge strap which at its ends is integrally connected to the cap and the top.

7. An apparatus for cleaning hoses used in the course of a dentist's work, comprising:
   (a) a container having a mouth through which fluid may be added to the container; and
   (b) a top adapted to snugly cover the mouth of the container, the top having
      (i) a nozzle protruding upwardly from a surface of the top to the exterior of the container, the nozzle having an internal bore through which fluid in the container may pass and the nozzle sized to fit snugly within a hose attachment attached firmly to the end of an external suction hose so that the hose may be connected to the nozzle via the hose attachment,
      (ii) a hollow internal tube attached firmly to the nozzle and extending into the lower interior portion of the container, such that fluid may be drawn by suction through the internal tube, the nozzle, and then the external hose;
   wherein an outer surface of the nozzle includes axially-oriented grooves extending the length of the nozzle so that when the hose attachment is placed over the nozzle, air gaps are formed between the outer surface of the nozzle and an inside surface of the hose attachment whereby the grooves prevent these surfaces from fully abutting against one another, whereby air may be drawn into an external hose along with fluid from the container to agitate the fluid.

8. The apparatus of claim 7 wherein a lower portion of an outer surface of the nozzle is widened in a radially outward direction to the flat surface of the top, such that the hose attachment encases an upper portion of the nozzle but not the lower portion of the nozzle.

9. An apparatus for cleaning hoses used in the course of a dentist's work, comprising:
   (a) a container having a mouth through which fluid may be added to the container; and
   (b) a top adapted to snugly cover the mouth of the container, the top having
      (i) a nozzle protruding upwardly from a surface of the top to the exterior of the container, the nozzle having an internal bore through which fluid in the container may pass and the nozzle sized to fit snugly within a hose attachment attached firmly to the end of an external suction hose so that the hose may be connected to the nozzle via the hose attachment, wherein a lower portion of an outer surface of the nozzle is widened in a radially outward direction to the flat surface of the top, such that the hose attachment encases an upper portion of the nozzle but not the lower portion of the nozzle; and
      (ii) a hollow internal tube attached firmly to the nozzle and extending into the lower interior portion of the container, such that fluid may be drawn by suction through the internal tube, the nozzle, and then the external hose,
   wherein the outer surface of the nozzle includes axially-oriented grooves extending through both the upper portion and lower portion of the nozzle so that when the hose attachment encases the upper portion of the nozzle, air gaps are formed between the outer surface of the upper portion of the nozzle and the inside surface of the hose attachment whereby the grooves prevent these surfaces from fully abutting against one another, thereby allowing air to enter the hose attachment through the air gaps without obstruction.

10. An apparatus for cleaning hoses used in the course of a dentist's work, comprising:
   a) a container having a mouth through which fluid may be added to the container; and
   b) a top adapted to snugly cover the mouth of the container, the top having
      i) a high volume suction (HVS) nozzle protruding upwardly from a surface of the top to the exterior of the container, the HVS nozzle having an internal bore through which fluid in the container may pass and the HVS nozzle sized to fit snugly within a HVS hose attachment attached firmly to the end of an external HVS hose so that the HVS hose may be connected to the HVS nozzle via the HVS hose attachment,
      ii) a low volume suction (LVS) nozzle protruding upwardly from the surface of the top to the exterior of the container, the LVS nozzle having an internal bore through which fluid in the container may pass and the LVS nozzle sized to fit snugly within a LVS hose attachment attached firmly to the end of an external LVS hose so that the LVS hose may be connected to the LVS nozzle via the LVS hose attachment, and
      iii) a separate internal tube attached firmly to each nozzle and extending into the lower interior portion of the container, such that fluid may be drawn by suction through the internal tubes, the HVS and LVS nozzles, and then the HVS and LVS hoses,
   wherein an outer surface of the HVS nozzle includes axially-oriented grooves extending the length of the HVS nozzle so that when the HVS hose attachment is placed over the HVS nozzle, air gaps are formed between the outer surface of the HVS nozzle and an inside surface of the HVS hose attachment whereby the grooves prevent these surfaces from fully abutting against one another; and
   wherein an outer surface of the LVS nozzle includes axially-oriented grooves extending the length of the LVS nozzle so that when the LVS hose attachment is placed over the LVS nozzle, air gaps are formed between the outer surface of the LVS nozzle and an inside surface of the LVS hose attachment, whereby the grooves prevent these surfaces from fully abutting against one another.

11. The apparatus of claim 10 wherein the container includes a handle for carrying the apparatus.

12. The apparatus of claim 10 wherein the container includes markers on the side of the container, each marker being labelled to indicate the volume of fluid in the container when the container is filled to the height of the markers.

13. The apparatus of claim 10 wherein the top has threads for screwing the top onto the container mouth and the mouth has threads adapted to receive the threads on the top, so that rotation of the top in one direction rotates the top onto the threaded mouth to close and seal the container, while rotation of the top in an opposite direction causes the top to be loosed from the mouth.

14. The apparatus of claim 10 wherein the top has a flat surface with an aperture therein such that the container may be filled with fluid either by adding fluid through the mouth of the container or by adding fluid through the aperture in the top.

15. The apparatus of claim 10 wherein the top has a flat surface and a lower portion of the outer surface of the HVS nozzle is widened in a radially outward direction to the flat surface of the top, such that the HVS hose attachment incases an upper portion of the HVS nozzle but not the lower portion of the HVS nozzle; and
wherein a lower portion of the outer surface of the LVS nozzle is widened in a radially outward direction to the flat surface of the top, such that the LVS hose attachment encases an upper portion of the LVS nozzle but not the lower portion of the LVS nozzle.

16. An apparatus for cleaning hoses used in the course of a dentist's work, comprising:
 a) a container having a mouth through which fluid may be added to the container; and
 b) a top adapted to snugly cover the mouth of the container, the top having
  i) a high volume suction (HVS) nozzle protruding upwardly from a surface of the top to the exterior of the container, the HVS nozzle having an internal bore through which fluid in the container may pass and the HVS nozzle sized to fit snugly within a HVS hose attachment attached firmly to the end of an external HVS hose so that the HVS hose may be connected to the HVS nozzle via the HVS hose attachment,
  ii) a low volume suction (LVS) nozzle protruding upwardly from the surface of the top to the exterior of the container, the LVS nozzle having an internal bore through which fluid in the container may pass and the LVS nozzle sized to fit snugly within a LVS hose attachment attached firmly to the end of an external LVS hose so that the LVS hose may be connected to the LVS nozzle via the LVS hose attachment, and
  iii) a separate internal tube attached firmly to each nozzle and extending into the lower interior portion of the container, such that fluid may be drawn by suction through the internal tubes, the HVS and the LVS nozzles, and then the HVS and LVS hoses, wherein the top has a surface with an aperture such that the container may be filled with fluid either by adding fluid through the mouth of the container or by adding fluid through the aperture in the top, and further including
  iv) a lip surrounding and extending upwardly from the aperture, the lip having a gradually increasing outside diameter where the largest diameter is located at an uppermost portion of the lip;
  v) a cap having a planar portion and a cylindrical surface integrally connected to and extending downward from the planar portion, the cylindrical surface having a gradually decreasing inside diameter where the smallest diameter is located at a bottom cylindrical portion which engages the lip first; and
 wherein the largest outside diameter of the lip is slightly greater than the smallest inside diameter of the cylindrical surface of the cap so that the application of a moderate amount of downward force to the cap when placed over the lip of the aperture causes resilient engagement of the lip.

17. The apparatus of claim 16 further including a hinge strap which at its ends is integrally connected to the cap and the top.

18. A method for cleaning hoses used in the course of a dentist's work, comprising the steps of:
 (a) adding cleaning fluid to a container having a mouth through which the fluid may be added;
 (b) sealing the container with a top adapted to snugly cover the mouth of the container, wherein the top includes
  (i) a nozzle protruding upwardly from a surface of the top to the exterior of the container, the nozzle having an internal bore through which the fluid in the container may pass and the nozzle sized to fit snugly within a hose attachment attached to the end of an external suction hose so that the hose may be connected to the nozzle via the hose attachment, the outer surface of the nozzle including axially-oriented grooves extending the length of the nozzle, and
  (ii) an internal tube attached firmly to the nozzle and extending into the lower interior portion of the container;
 (c) placing the hose attachment over the nozzle such that air gaps are formed between the outer surface of the nozzle and an inside surface of the hose attachment whereby the grooves prevent these surfaces from fully abutting against one another; and
 (d) applying suction to the external suction hose so that the fluid in the container is drawn through the internal tube, the nozzle, and then the hose, and air is drawn in through the air gaps between the nozzle and hose attachment thereby cleaning the hose with the cleaning fluid from the container.

19. The method as defined by claim 18, wherein the top has a flat surface with an aperture therein such that the step of adding cleaning fluid to the container may be performed by either adding fluid through the mouth of the container or by adding fluid through the aperture in the top.

20. A method for cleaning hoses used in the course of a dentist's work, comprising the steps of:
 (a) adding cleaning fluid to a container having a mouth through which the fluid may be added;
 (b) sealing the container with a top adapted to snugly cover the mouth of the container, wherein the top includes (i) a nozzle protruding upwardly from a surface of the top to the exterior of the container, the nozzle having an internal bore through which the fluid in the container may pass and the nozzle sized to fit snugly within a hose attachment attached to the end of an external suction hose so that the hose may be connected to the nozzle via the hose attachment, (ii) an internal tube attached firmly to the nozzle and extending into the lower interior portion of the container;

(iii) wherein the top has a surface with an aperture therein such that the step of adding cleaning fluid to the container may be performed by either adding fluid through the mouth of the container or by adding fluid through the aperture in the top, and wherein the step of sealing the container is carried out by covering the mouth of the container with the top adapted to snugly cover the mouth, and by covering the aperture with a cap adapted to resiliently engage a lip surrounding and extending upward from the aperture when a moderate amount of downward force is applied to the cap when placed over the aperture;

(c) placing the hose attachment over the nozzle; and (d) applying suction to the external suction hose so that the fluid in the container is drawn through the internal tube, the nozzle, and then the hose, thereby cleaning the hose with the cleaning fluid from the container.

* * * * *